| United States Patent [19] | [11] Patent Number: 4,915,946 |
|---|---|
| Kang | [45] Date of Patent: Apr. 10, 1990 |

[54] PROCESS FOR MANUFACTURING A FUSED SALT FROM GINKGO, PERSIMMON, PINE, AND BAMBOO, AND THE COMPOSITION PRODUCED THEREBY

[76] Inventor: Kwon J. Kang, 101-5 Nonhyun-Dong, Kangnam-Ku, Seoul, Rep. of Korea

[21] Appl. No.: 143,397

[22] Filed: Jan. 13, 1988

[30] Foreign Application Priority Data

Jul. 21, 1987 [KR] Rep. of Korea ............... 87-7884[U]

[51] Int. Cl.⁴ .................. A61K 35/78; A23L 1/30
[52] U.S. Cl. .................. 424/195.1; 424/196.1; 426/648; 426/649
[58] Field of Search ............... 426/648, 649; 424/195.1, 196.1

[56] References Cited

U.S. PATENT DOCUMENTS 2,689,794  9/1954  Jackson ........................ 426/648
4,683,140  7/1987  Kang ........................... 424/195.1 X

*Primary Examiner*—John W. Rollins
*Assistant Examiner*—W. Catchpole
*Attorney, Agent, or Firm*—Birch, Stewart, Kolasch & Birch

[57] ABSTRACT

Bay salt with Ginkgo, Persimmon, Pine and Bamboo are used to form an initial mixture with bay salt in a ratio of about 200:1 by weight percent. The mixture is placed in a special furnace, and then burned by using firewood of Ginkgo, Persimmon, Pine and Bamboo at a temperature of about 1,000° to 1,3000° C. to produce a solid salt ash. The solid salt ash is then repeatedly burned about 5 to 6 times in accordance with the above method to produce a burned solid salt ash. This burned solid salt ash is the put into a Bamboo tube and further burned with firewood of Ginkgo, Persimmon, Pine and Bamboo at about 1,000° to 1,300° C. Finally, the burned solid salt ash is put into an electric furnace, and heated at a temperature of about 1,3000° C. to manufacture the salt composition.

9 Claims, 4 Drawing Sheets

4,915,946

PROCESS FOR MANUFACTURING A FUSED SALT FROM GINKGO, PERSIMMON, PINE, AND BAMBOO, AND THE COMPOSITION PRODUCED THEREBY

BACKGROUND OF THE INVENTION

1. Field of the Invention

The present invention relates to a process for manufacturing a fused salt from natural substances, namely bay salt, Ginkgo, Persimmon, Pine and Bamboo, and the composition produced thereby. More particularly, the present invention relates to an evaporated salt composition utilizing ash from bay salt and leaves obtained from a combination of Ginkgo, Persimmon, Pine and Bamboo. Still further, the present invention pertains to an inflammatory treatment containing ash from bay salt which is a very coarse-grained variety of common salt originally obtained from sea water (hereinafter "bay salt") and the leaves of Ginkgo *biloba* L., *Diospyros Kaki* L., *Pirus monophylla*, and *Bambusa arundinacea*.

2. Description of the Prior Art

There are many types of known sodium chloride salts such as fine granulated salt, table salt, evaporated salt, iodized salt and the like. Also, there are many types of known tea made from natural substances such as persimmon and pine leaves. However, it has been heretofor unknown how to provide an evaporated salt made of ash from bay salt and leaves of Ginkgo, Persimmon, Pine and Bamboo.

SUMMARY OF THE INVENTION

Accordingly, it is an object of the present invention to provide a process for manufacturing an evaporated salt from bay salt, and leaves of Ginkgo, Persimmon, Pine and Bamboo.

Another object of the present invention is to provide an evaporated salt composition utilizing ash made from bay salt, and leaves of Ginkgo, Persimmon, Pine and Bamboo.

A further object of the present invention is to provide an inflammatory treatment containing ash formed from bay salt and leaves of Ginkgo, Persimmon, Pine and Bamboo at temperatures of about 1,000° to 1,300° C.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

In carrying out the present invention, Ginkgo, Persimmon, Pine and Bamboo are used to form an initial mixture with bay salt in a ratio of about 200:1 by weight percent. The mixture is placed in a special furnace, and then burned by using firewood of Ginkgo, Persimmon, Pine and Bamboo at a temperature of about 1,000° to 1,300° C. to produce a solid salt ash. The solid salt ash is then repeatedly burned about 5 to 6 times in accordance with the above method to produce a burned solid salt ash. This burned solid salt ash is then put into a Bamboo tube and further burned with firewood of Ginkgo, Persimmon, Pine and Bamboo at about 1,000° to 1,300° C. Finally, the burned solid salt ash is put into an electric furnace, and heated at a temperature of about 1,300° C. to manufacture the salt composition of the present invention.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Referring now in detail to the preferred embodiments of present invention and to the drawings for the purpose of illustrating preferred embodiments of the present invention, there is provided by the present invention a remedial salt composition for use in a medicinal food. The medicinal food salt composition of the present invention is made from natural substances, namely bay salt, Ginkgo, Persimmon, Pine and Bamboo.

Figure 1:
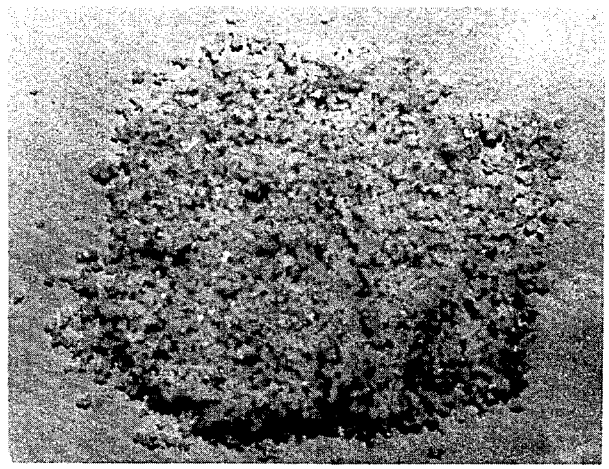
FIG. 1 is an enlarged picture of the prior art bay salt.
Figure 2:
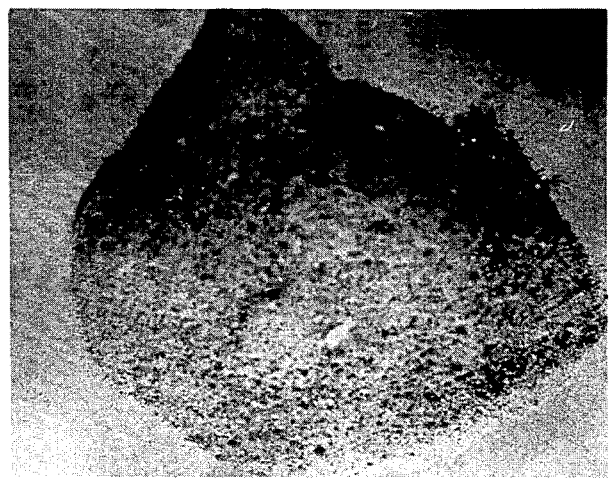
FIG. 2 is an enlarged picture of an ash-salt obtained from the third step of the present invention.
Figure 3:
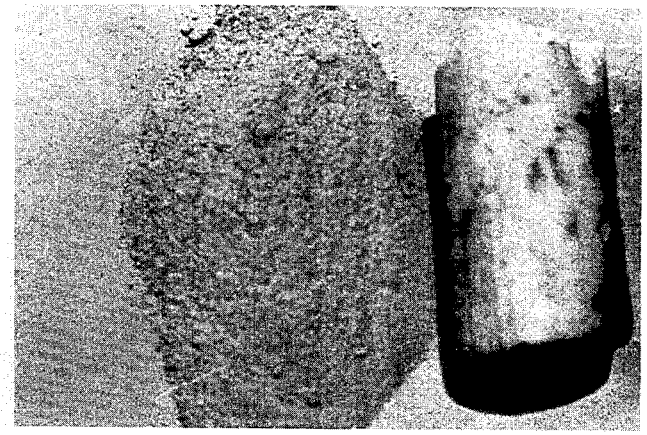
FIG. 3 is an enlarged picture of a solid salt obtained from the fourth step of the present invention.
Figure 4:
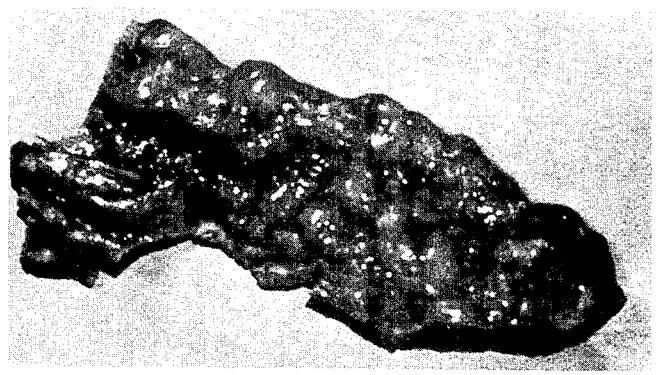
FIG. 4 is an enlarged picture of a solid salt obtained from the fifth step of the present invention.
Figure 5:
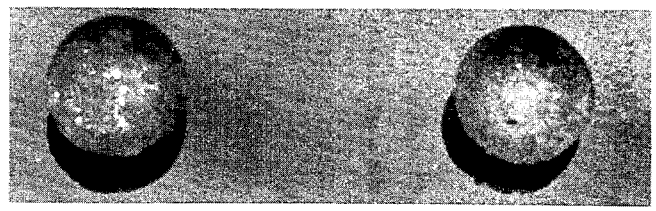
FIG. 5 is enlarged pictures of solved salt of the prior art bay salt at temperature of 900°–1,000° C. (left side) when compared with the fused salt at a temperature of 400°–600° C. of the present invention.
Figure 6:
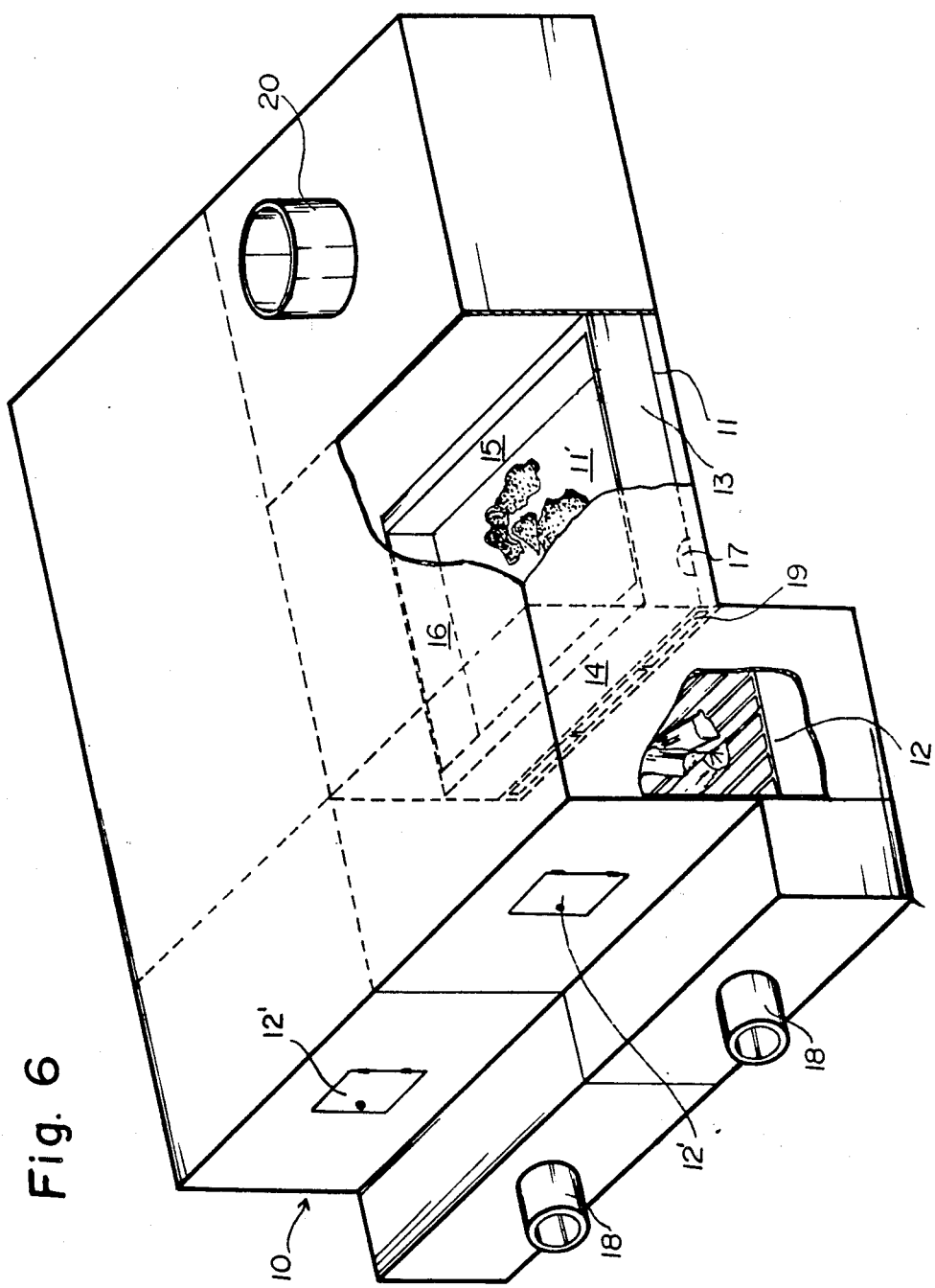
FIG. 6 is a perspective view of a furnace of the present invention.

Initially, untreated bay salt as shown in FIG. 1 is heated in a combustion container 11 disposed in a furnace 10 as shown in FIG. 6 at a temperature of about 400° to 600° C. to produce an evaporated salt powder. During this heating, the three doors 14, 15 and 16 are closed. This evaporated powder salt is then combined with leaves from natural substances to form an initial mixture. The leaves are prepared by cutting a quantity of dry leaves from the Ginkgo, Persimmon, Pine and Bamboo families at a size of about 200 mesh. The Ginkgo, Persimmon, Pine and Bamboo leaves are provided in equal amounts by weight, with respect to each other. The quantity of the evaporated salt powder to be combined with the leaves from the genus Ginkgo, Persimmon, Pine and Bamboo used is in an amount of about 95% of salt as compared to 5% by weight of leaves. In one preferred embodiment, 10 kg of bay salt in the form of the evaporated salt powder and 500 g of the leaves from natural substances are combined in an initial mixture.

In a second step, as shown in FIG. 6, the initial mixture is put into the furnace 10. That is, the initial mixture is placed in a combustion container 11 having air inlets 18 and firewood from Ginkgo, Persimmon, Pine and Bamboo wood is placed in a fireplace 12 having doors 12'. The combustion container 11 comprises a panel 11' disposed at the bottom thereof, front, rear and left side doors 14, 15 and 16, and a solution outlet 17 disposed at the bottom of a right side wall 13. At this time, the front and rear doors 14 and 15 are closed and the left side door 16 is opened. When the firewood is burned using fresh air through the air inlets 18, the fire passes through a fire tunnel 19 to a chimney 20. At this time, the temperature in the initial mixture may be measured about 1,000° to 1,300° C. and natural minerals such as sulfur, potassium, or the like from the fire wood are combined with the initial mixture so that most of the fusing solution is discharged through the solution outlet 17 and little fusing solution is evaporated away through the chimney 20. The fusing solution from the solution outlet 17 is immediately solidified to obtain a black fused salt.

In a third step, the black fused solid is pulverized in a conventional pulverizer to obtain a powder therefrom. The same quantity of untreated dry leaves as used in the initial first step described above is then added to the pulverized powder. The combustion procedure of the above-described second step of the present invention is then repeated. The present third step is then repeated about 5 to 6 times to obtain a pulverized final product containing a large quantity of minerals therein.

Figure 8:
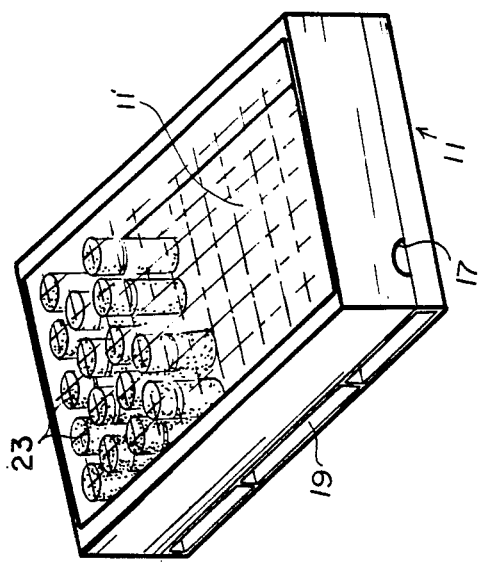
FIG. 8 is a perspective view of a panel containing a plurality of solid salt rods.
Figure 7:
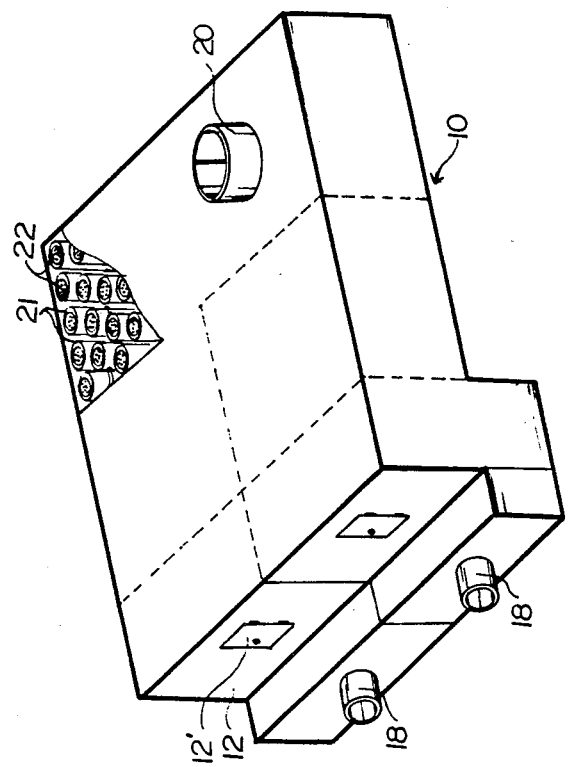
FIG. 7 is a perspective view of a furnace containing a plurality of Bamboo tubes with the evaporated salt of the present invention.

In a fourth step, the pulverized powder 22 from the third step is put into a plurality of Bamboo wood tubes 21 and the plurality of Bamboo wood tubes 21 are stood on end in the combustion container 11 which is placed in the furnace 10 as shown in FIG. 7. At this time, firewood from Ginkgo, Persimmon, Pine and Bamboo is utilized as a solid fuel for burning the Bamboo wood tubes which contain the pulverized powder rod. This process results in forming a solid salt rod 23 in the combustion container 11 of the furnace 10 as shown in FIG. 8.

In a fifth step, the plurality of solid salt rods 22 are put into the combustion container 11 in the furnace 10 and heated with the firewood at a temperature of about 1,000° to 1,300° C. for fusion and discharge through the solution outlet 17. The fusing solution becomes a black fused solid product in the atmosphere.

In a sixth step, the black fused solid product is placed in an electric furnace and heated to a temperature of about 400° to 600° C. at which point the final fusing begins. Thereafter, the temperature increases until about 1,300° C. and impurities contained in the solid product are completely combusted thereby purifying the product. Conventional untreated bay salt normally starts to fuse at a much higher temperature of about 900° C. when compared with that of the product of the present invention. This indicates a difference in properties between the product of the present invention and conventional untreated bay salt. The final product of the present invention can then be granulated for use as a salt tablet or the like.

The present invention will now be described in more detail in connection with the following examples which should be considered as being exemplary and not limitative of the present invention.

EXAMPLE 1

Tablet

The final purified product resulting from the above-described process is manufactured as a tablet, wherein each tablet contains 1 g of the purified product. This tablet is useful for treating inflammatory disease in the mouth such as caries, gumboil, tonsilitis, asthma, and the like.

EXAMPLE 2

Solution 1 g of the final purified product is dissolved in 100 ml of sterile distilled water and is filtered to obtain filtrate for use in eye, nose and ear diseases. The solution can also be utilized as a mouthwash.

EXAMPLE 3

Ointment

The purified product is mixed with a conventional ointment base to treat dermatitis, eczema, athlete's foot and hemorrhoids.

Table I shows an analysis of the elements in the final purified product of the present invention when compared with a conventional bay salt disclosed by the prior art as follows:

TABLE I

|  | A fused salt produced by the present invention | A conventional bay salt |
|---|---|---|
| NaCl | 96% | 99.84% |
| Ca | 0.16% | 0.03% |
| Mg | 0.56% | 0.006% |
| S | 0.88% | 0.074% |
| Fe | 130 ppm | 0.5 ppm |
| Cu | 5 ppm | 0.14 ppm |
| Na | 37.2% | 39.2% |
| Cl | 58.8% | 60.6% |

As shown in Table I, the fused salt according to the present invention which was analyzed was acquired at Korea Advanced Institute of Science and Technology, Seoul, Korea.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing a fused salt composition which comprises the steps of:
   (a) heating a predetermined quantity of bay salt at an elevated temperature to form a salt powder;
   (b) combining said salt powder with leaves from the genus Ginkgo, Persimmon, Pine and Bamboo to form an initial mixture, said salt powder and said leaves being present in amount of about 95% and 5% by weight, respectively;
   (c) combusting said initial mixture in a furnace using firewood at a temperature of about 1,000° to 1,300° C. to produce a first fusing solution which is solidified into a first fused solid;
   (d) pulverizing said fused solid to form a pulverized solid;
   (e) combusting a mixture formed from combining said pulverized solid with leaves from the genus Ginkgo, Persimmon, Pine and Bamboo in said furnace with firewood at a temperature of about 1,000° to 1,300° C. to produce a second fusing solution which is solidified into a second fused solid;
   (f) repeating steps (d) and (e) at least 5 times;
   (g) combusting a plurality of Bamboo tubes which contain said fused solid produced by step (f) in said furnace to produce solid salt rods;

(h) heating said solid salt rods in said furnace at a temperature of about 1,000° to 1,300° C. to produce a third fusing solution which is solidified into a third fused solid; and (i) heating said third fused solid in an electronic furnace to a temperature of about 1,300° C. to form a final fused salt composition.

2. The process for preparing a fused salt composition of claim 1, wherein the genus Ginkgo is *Ginkgo biloba* L.

3. The process for preparing a fused salt composition of claim 1, wherein the genus Persimmon is *Diospyros kaki* L.

4. The process for preparing a fused salt composition of claim 1, wherein the genus Pine is *Pinus monophylla*.

5. The process for preparing a fused salt composition of claim 1, wherein the genus Bamboo is *Bambusa arundinacea*.

6. The process for preparing a fused salt composition of claim 1, wherein the bay salt is heated in step (a) at a temperature of 400° to 600° C.

7. The process for preparing a fused salt composition of claim 1, wherein the firewood comprises wood from Ginkgo Persimmon, Pine and Bamboo trees.

8. The process for preparing a fused salt composition of claim 1, wherein the furnace includes a combustion container having a front door, a rear door, a left side door, and a right side wall, wherein said front door includes a fire tunnel which allows for minerals from the combusting firewood to combine with the fusing solution and said right side wall has a solution outlet formed therein for discharging the fusing solution so that most of the fusing solution is discharged and little of it is evaporated away.

9. A fused salt produced by the process of claim 1.

* * * * *